United States Patent
Miller (12)

(10) Patent No.: US 6,297,719 B1
(45) Date of Patent: Oct. 2, 2001

(54) MAGNET SET FORMING AND ALIGNING APPARATUS AND METHOD

(76) Inventor: Craig Miller, 6092 Ohio St., Yorba Linda, CA (US) 92886

( * ) Notice: Subject to any disclaimer, the term of this patent is extended or adjusted under 35 U.S.C. 154(b) by 0 days.

(21) Appl. No.: 09/633,317

(22) Filed: Aug. 7, 2000

(51) Int. Cl.[7] ....................................................... H01F 7/02
(52) U.S. Cl. ............................................ 335/306; 210/222
(58) Field of Search ............................ 335/284, 302–306; 224/183; 210/222

(56) References Cited

U.S. PATENT DOCUMENTS

| | | | |
|---|---|---|---|
| 4,486,729 | * 12/1984 | Lee | 335/306 |
| 4,509,219 | * 4/1985 | Yagi. | |
| 4,587,956 | * 5/1986 | Griffin et al. . | |
| 4,921,560 | * 5/1990 | Yamaguchi . | |
| 5,063,368 | * 11/1991 | Ettehadich | 335/304 |
| 5,596,304 | * 1/1997 | Tatchyn | 335/306 |

* cited by examiner

Primary Examiner—Lincoln Donovan

(57) ABSTRACT

An apparatus and method for initially bringing together and thereafter delivering an aligned set of magnets easily separable into sets of 4 or higher in even numbers. While magnetic units are effective in magnetic therapy where a relatively flat surface is to be applied toward the skin surface, the side by side arrangement of magnets with a cross section substantially greater than the thickness results in attractive and repulsive forces in the four magnet magnetic unit such that the set is easily fragmented after bringing them together unless the unit is immediately supportively encapsulated. Such encapsulation includes sealed polymer envelopes with sufficient lateral and torsional rigidity to keep the magnets in the unit in the desired square planar arrangement instead of stacking, overlapping or flipping polar sides while at the same time having planar flexibility to be applied to undulating skin surfaces so that the skin side face of the individual magnets are substantially normal to the skin surface to deliver a maximum Gaussian field.

5 Claims, 3 Drawing Sheets

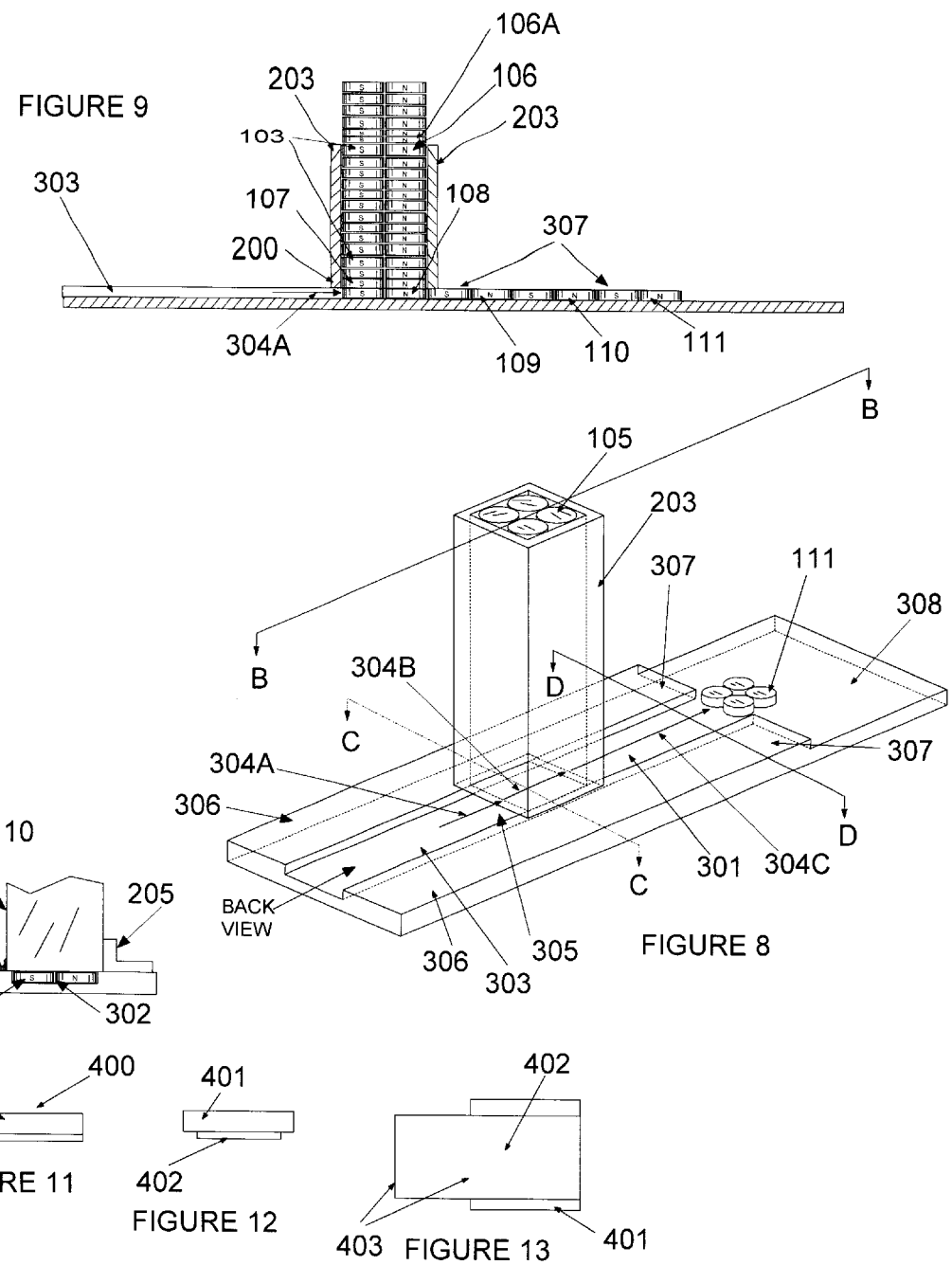

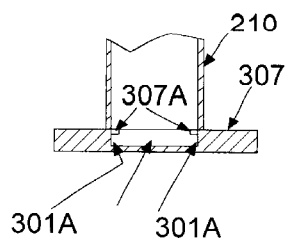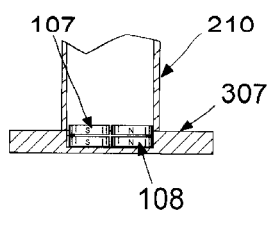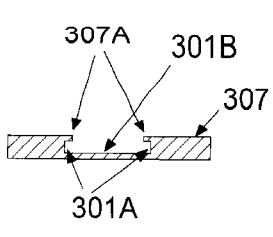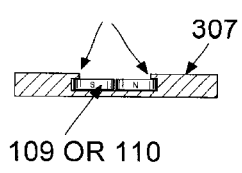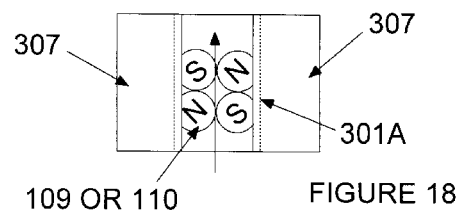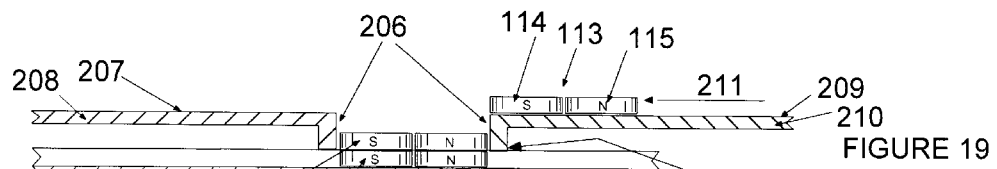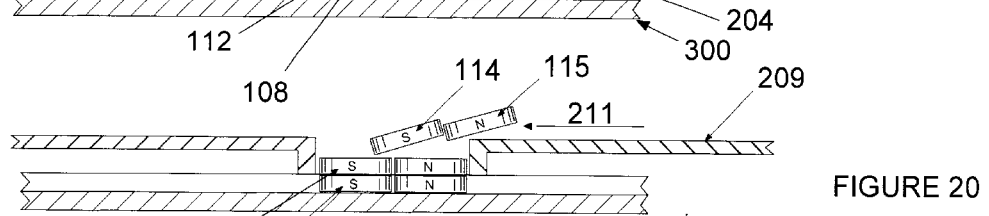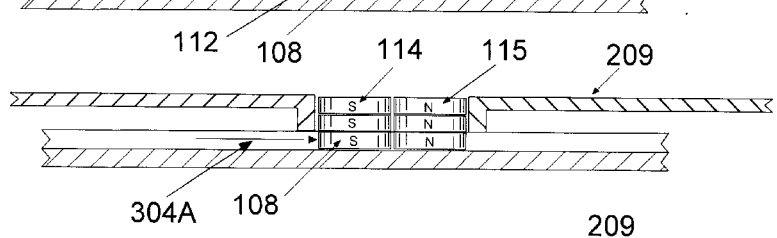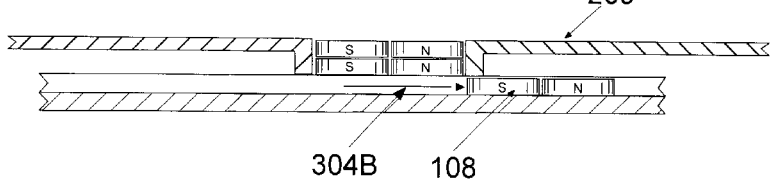

MAGNET SET FORMING AND ALIGNING APPARATUS AND METHOD

BACKGROUND OF THE INVENTION

The present invention relates to magnets arranged in sets and aligned for encapsulation into magnetic therapy devices.

Magnetic therapy practice has caused the development of products with permanent magnets distributed on the products. For example, U.S. Pat. No. 4,509,219 teaches a sleeping mattress structure provided with permanent magnets each having a magnetic field strength of at least 850 gauss which are disposed on the mattress for maximum magnetic curing effect. U.S. Pat. No. 4,921,560 teaches a method for fixing the permanent magnets to bed covering. Merchandise worn by humans having magnetic structure has also been developed. For example, Japan Life Products 1992 Catalog, at page 10 and 11, show belts, elbow and knee supporters, wrist and foot support massager provided with magnetic structure. Similarly, present day magnetic therapy merchandise includes head bands, vests, belts, wrist bands, supports for the elbows, arms, legs, knee and ankle, and also necklaces.

The apparent premise for the merchandise provided with the magnetic structure is to place a permanent magnet such that body cells are exposed to a low-level magnetic field emitted from the permanent magnets. The magnetic exposure is believed to assist stressed cells in restoring their correct balance of electrical charge for performing more efficiently, see undated article by Japan Life Products, entitled: "Spreading Good Sleep Around the World". The magnetic exposure when concentrated at the same specific points on the body known to acupuncture and accupressure practitioners is a developing therapeutic practice.

An especially effective form of an arrangement of magnets for application to directly on the human skin, or within one to two layers of natural or synthetic material or sheet polymer, has been shown to be a set of magnets of about the same cross sectional area is several permanent magnets are required to produce the maximum magnetic exposure.

In U.S. Pat. No. 4,587,956 it is disclosed that opposite magnetic poles have unique therapeutic effects on body tissues. That patent discloses that flux from a north pole of a magnet if applied in effective levels in the order of at least 200 gauss per square inch has a sedator effect, reduces pain, mobilizes calcium, relieves muscle spasms, increases joint mobility and lowers the pH of the affected tissues. By contrast, flux from a south pole of a magnet stimulates circulation, speeds healing time, strengthens tissues, and raises the pH to a weak alkaline condition characterizing healthy tissue. It is further disclosed that the north pole flux may reduce the electrogalvanic potential across the nerve sheaths in the affected tissue to a value substantially below that recognized by the brain as a pain signal; and that the south pole flux, if applied subsequently, does not raise the potential to a value which the brain would recognize as a pain signal, thus it can effect healing while enabling normal exercise without pain.

A prior art arrangement of magnets is known to engage the cooperative magnetic strength of side by side magnets and to at the same time provide enhanced equal and opposite polar magnetic effects. FIGS. 1–3 are exemplary of these arrangements, referred to herein as a magnetic unit.

SUMMARY OF THE INVENTION

The present invention comprises an apparatus and method for initially bringing together and thereafter delivering an aligned set of magnets easily separable into sets of 4 or higher in even numbers. While magnetic units are effective in magnetic therapy where a relatively flat surface is to be applied toward the skin surface, the side by side arrangement of magnets with a cross section substantially greater than the thickness results in attractive and repulsive forces in the four magnet magnetic unit as in FIGS. 1–3 such that the set is easily fragmented after bringing them together unless the unit is immediately supportively encapsulated. Such encapsulation includes sealed polymer envelopes with sufficient lateral and torsional rigidity to keep the magnets in the unit in the desired square planar arrangement instead of stacking, overlapping or flipping polar sides while at the same time having planar flexibility to be applied to undulating skin surfaces so that the skin side face of the individual magnets are substantially normal to the skin surface to deliver a maximum Gaussian field. Clearly, the assembly of the unit and transfer to a sufficiently supportive encapsulation are in the prior art a labor intensive activity, where the magnets are brought together by hand to assure correct polar relation in the unit and afterward each unit is moved to an encapsulation bottom sheet in a way to maintains the planar and polar relation of the unit. Where the very strong rare earth permanent magnets are used, the planar arrangement maintenance is an absolute requirement as such magnets are virtually impossible to separate face to face in opposite pole arrangement without some tool. There is a need for a device and method that will reduce the hand work and time needed to accomplish these steps.

The present invention is a plenum or chute into which are fed or stacked one planar unit after another. In this description, magnets have a substantial cross section greater than the magnet thickness, forming sides and top and bottom cross section faces having generally about the same area and shape in a unit. Poles of the magnet are located on the faces and reference to poles in this description refers to the pole of the top face. Stacking in the plenum of the units is such that the pole of a top face is opposite the pole of the bottom face of the unit just above it. Thus, the units are attractively held together in a stack which may rise to a substantial height above the side supportive chute or plenum without the need of such side support.

The side support of the chute or plenum is required only for a penultimate unit, the next to the bottom unit of a stack of two or more units, where at least the next to the bottom unit is actually within the cross section of the chute or plenum. A slider space is formed beneath the chute or plenum having about the dimensions of a unit immediately below the next to the last unit bottom unit, where the slider space is defined by a floor and at least two side walls. A bottom unit is by gravity pressed into that slider space by the weight of the units above it. A slider or other motion inducing means (magnetic, finger projections from slots in the floor, etc.) moves the bottom unit from the slider space to a delivery slot portion, whereby retraction of the slider from the slider space causes the previously next to the bottom unit to drop into the slider space to become the bottom unit. Successive actions of moving the slider into and retracting from the slider space causes a succession of units to move into the delivery slot portion, forming two rows of magnets having adjacent magnets with opposite (attracting) poles.

At an end of the delivery slot portion, each motion of the slider into the slider space pushes a unit free of the walls of the delivery slot portion onto a flat assembly surface. In one preferred embodiment, a flat circular piece of metal (such as a 0.25 to 1.5 inch diameter washer) is lain on the top of the unit touching the top of each individual magnet such that it forms a magnetic field condenser and provides planar maintenance support to the unit. The

BRIEF DESCRIPTION OF THE DRAWINGS

FIG. 8 shows a top oblique view of an embodiment of the invention plenum holding magnetic units supportively deliverable to a slider slot portion below the plenum whereafter a magnetic unit is moved into a delivery slot portion.

FIG. 9 is a cross section BB view of FIG. 8. FIG. 10 is an end view of FIG. 8.

FIGS. 11–13 are respectively side, end and bottom views exemplary of the invention slider movable in the slider slot of portion FIG. 8 to sequentially deliver to the delivery slot portion aligned magnetic units.

FIGS. 14–18 are alternate embodiments of the present invention as to the delivery slot portion.

FIGS. 14 and 15 are slider slot portions for the alternate embodiment as cross sections CC of FIG. 8 respectively showing the slider slot portion without and with a magnetic unit.

FIGS. 16 and 17 are delivery slot portions for the alternate embodiment as cross sections DD of FIG. 8 respectively showing the delivery slot portion without and with a magnetic unit.

FIG. 18 is a top view of FIG. 17.

FIGS. 19–22 are an alternate embodiment of the invention plenum for assembling individual magnets into a magnetic unit at the top of the invention plenum.

FIGS. 19–22 show a cross section similar to that of FIG. 9 whereby the plenum is reduced to the height of three or more magnetic units and a sorting surface is made intregral with the plenum top opening, whereby a sequence of respectively sorting, plenum insertion, plenum support and slider delivery are shown.

DETAILED DESCRIPTION OF THE INVENTION

The invention is now discussed with reference to the Figures.

Figure 1:
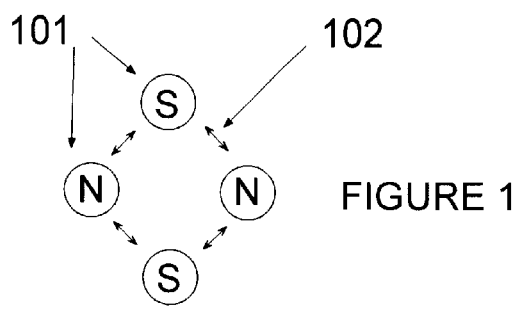
FIGS. 1–3 are respectively top separated, top brought together and top oblique views of 4 cylindrical sections of magnetized material having their cylinder tops arranged so that diagonal cylinders tops are of the same, opposing poles and side by side cylinders tops are of opposite, attracting poles, thereby forming a magnetic unit.
Figure 2:
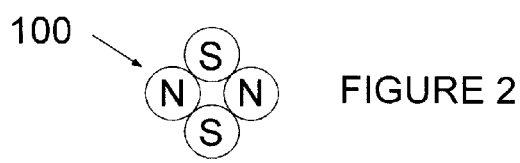
Figure 3:
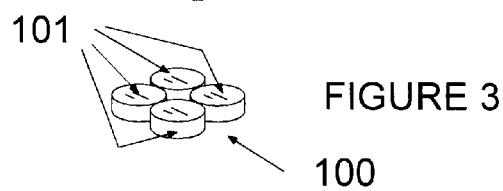

A current form of a 'magnet pack' of four side by side magnets is shown in FIGS. 1–3. For short cylindrical magnets 101, with a cross section diameter of from about less than about 0.25 inches to above about 1½ inches and a thickness of less than about 0.5 inches, are arranged so that their square 'set' 100 is maintained by the adjacency of opposite poles causing attractions 102. Thus, the set 100, unless in contact with magnetizable surfaces, tends to remain together on a table top or horizontal surface. However, in mass production, bringing into side by side relation more than one set clearly is a disadvantage—the magnets of the other set tend to either repel or attract the magnets of a nearby set and thereby disaggregating the sets and requiring hand re-assembly of the sets. Thus, an uneconomical amount of space and hand work is required to assemble the sets for encapsulating in a sufficiently rigid polymer or other containing means so that the set 100 magnets do not simply fall out of the planar alignment and disturb the Gaussian field concentration of that planar arrangement for substantially flexible body surface application of the set.

Each set 100 typically has applied to a top side a flat metal piece such as a washer with an outside diameter less than the plane width of the set 100 for enhancement of the collective magnetic field and for additional planar support, encapsulated as just described, and then combined in a supportive way to some flexible sheet material so that the material may be brought into close proximity to the curved surface of a human body for magnetic therapy treatment. The formation and assembly segregation of sets 100 has in the prior art required the use of all hand labor. The present invention provides a device for eliminating much of the space and hand labor required for that activity.

Figure 4:
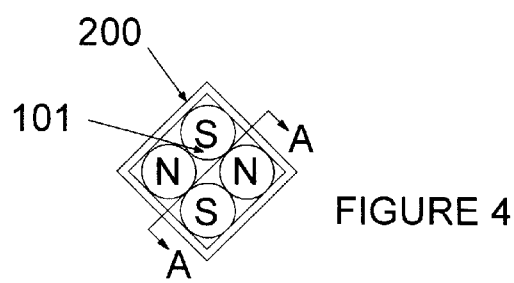
FIGS. 4 and 5 are top views are respectively the invention device holding one or more magnetic units in support plenum.
Figure 5:
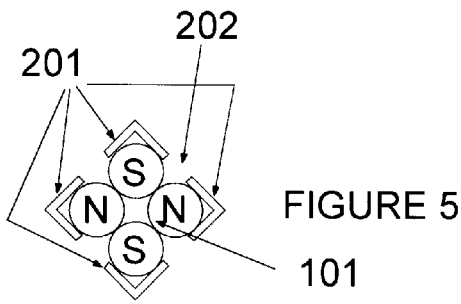

FIGS. 4 and 5 show top views of plenums 200. FIG. 5 plenum 200 comprises substantial slotting on the sides. The inside circumference of plenum 200 is adapted to contact sufficient of the lateral edges of the magnets of set 100 so that a substantially horizontal orientation is maintained as required for the segregated set. The underlying support for each set to maintain the horizontal relationship is either another set having its adjacent poles opposite to the above set or a sliding surface as disclosed below.

Figure 6:
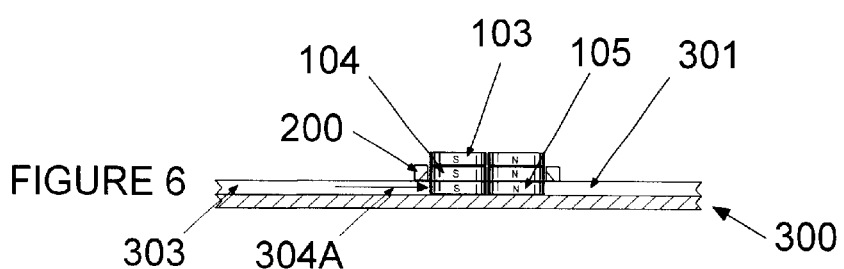
Figure 7:
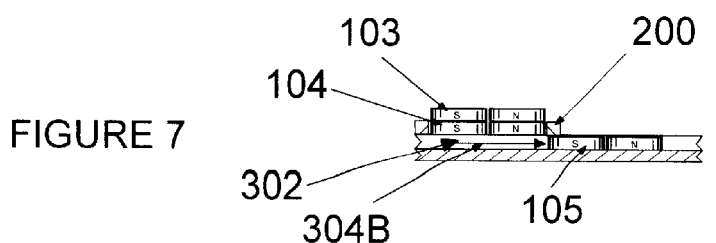

In a minimum plenum height of the invention, FIGS. 6 and 7 show a plenum 200 with a height of the thickness of one set. In this case, the set 104 is sandwiched between set 103 above and 105 below. The sequence of vertically opposing poles as described above are shown in the side view Figures with an "S" or "N" on the side of the individual magnets, such letter indicating the polarity of the top end of the magnet. It is understood that the non-magnet surfaces described for the invention device are preferably non-magnetic although sufficient rigid to accomplish the ends of the invention.

In FIG. 6, the stack of three sets 103–105 are supported in part in a stack by their own magnetic attraction. Several other sets may be applied to the top of set 103 in FIGS. 6 and 7 while obtaining the objects accomplished by the invention of those Figures. Plenum 200 is firmly attached on the bottom edges of two of its sides so it straddles slot section 302 of a slotted plate support 300 so that at least one opening is formed between slot sections 301 and 302, preferably also forming an opening between slot sections 302 and 303. FIGS. 6 and 7 show that slot sections 301–303 form a continuous slot. Section 302 is adapted to be just about the width of the inside diameter of the straddling plenum 200.

Either hand labor or tube delivery will be used to deliver the individual magnets into sets at the top of the stack of sets within and optionally above the plenum for the invention device and process. When, at a minimum, set 105 lies within section 302 and is pressed thereto by gravity and by set 104, motion 304A is initiated against a back lateral side of set 105. Motions 304A–304C may be accomplished with several means, although it is preferable to use a pressure face about less than the height and width of the slot of the slotted surface pushed. FIGS. 11–13 show a preferred hand slidable piece 400 having cross section dimensions of the slot sections 301–302 for piece 402 and a hand grasping piece 401 with somewhat wider cross section. Portion 403 of piece 400 comprises a front pushing face and a length about the slot axis outside diameter of plenum 200 (or 203). Motion 304A is continued through motion 304B such that set 105 (in FIG. 7) is moved out of section 302 into section 303, thereby leaving open section 302 whereupon set 104 drops into the section 302 previously occupied by set 105. Repetition of the motions 304A and 304B cause section 303 to fill with sets adjacent only on one side where such sets share opposite poles as to their top and bottom adjacent sides.

FIGS. 8 and 9 more clearly show this action. Plenum 203 is noticeably taller than plenum 200 and has within it sets 106 and above it sets 106A. The last set of the sets 106 is set 107 and the set within section 302 is set 108. Three previous actions of motions 304A and 304B resulted in the moving of sets 109 and 110 into slot section 303. Slotted surface 300 comprises back top surfaces 306 separated by slot section 303 and front top surfaces 307 separated by slot section 301, wherebetween such sections 301 and 303 is section 302 which is straddled by plenum 203, the plenum bottom being attached firmly by weld 204 or bracket 205 as in FIG. 10. Surface 300 further comprises runout surface 308 having an opening to an end of slot section 301 whereupon the sets may be moved to an encapsulation step. In FIGS. 8 and 9, set 111 has emerged from the confines of the section 301 after being pushed along by the successive motions 304A and 304B resulting in motion 304C. The length of section 301 may be many times that of FIGS. 8 and 9 to accommodate dozens of sets. The back and forth motion of slider 400 from section 303 to section 302 and back to section 303 transforms a vertical stack of sets into a horizontal adjacent line of single sets that are then quickly and efficiently moved to encapsulation.

Alternately, section 301 comprises several removable and replaceable sections so that the segregated and horizontally aligned sets may be carried to a remote encapsulation stage. When removeable sections of section 301 fill with sets, the sections can be removed and empty sections of section 301 put in their place.

FIGS. 14–18 define an alternate embodiment of section 301. Sections 301–303 are made deeper by the thickness of lips 307, which extend inward only along the upper edges of section 301 so that sets 109 or 110 of FIGS. 8 and 9 are less likely to be disturbed by a jolting of a table or other support for surface 300. The sets are further restrained by the lips 307 until they emerge onto surface 308. This also permits placement of the desireable pieces of flat metal on the sets prior to encapsulation.

FIGS. 19–22 show an improvement in the above invention device. An assembly support 210 with surface 209 is engaged about the top opening of plenum 206, forming thereby a rimless and horizontal surface and approach to that opening. A set 113 is composed of magnet pairs 114 and 115. This set was assembled by hand manipulation of scattered individual magnets on surface 209, as other subsequent sets can be assembled for loading into plenum 206. In FIG. 19, sets 108 and 112 are the section 302-located and next up in the stack sets, wherebefore a successive motions 301A and 301B have caused the vacancy space shown in plenum 306 above set 112. In FIG. 19, motion 211 is initiated whereby pair 114 has polarity opposite that of the adjacent aligned pair of magnets of set 112. Thus, as seen in FIG. 20, pair 114 is repelled over that immediately adjacent pair of set 112 and is attracted in opposite polarities to the next adjacent pair of magnets, whereby pair 115 is attractively moved and secured within plenum 206, as shown in FIG. 22.

The above design disclosures present the skilled person with considerable and wide ranges from which to choose appropriate obvious modifications for the above examples. However, the objects of the present invention will still be obtained by the skilled person applying such design disclosures in an appropriate manner.

I claim:

1. A device for changing the orientation of planar magnet sets from a substantially vertical stack to a substantially horizontal line of adjacent sets comprising:

(a) each set comprising four flat and substantially identical magnets having lateral sides and magnetic poles on top and bottom sides, the magnets arranged adjacently to their lateral sides such that immediately adjacent magnets have opposite magnetic polarities at their top and bottom poles;

(b) a plenum defining a chute with an axis and having a cross section adapted to laterally engage sets of plenum-axially supported sets, the plenum further defining a top and bottom opening of the chute and containing at least one set at just above the bottom opening;

(c) a plate defining a slot on an upper surface, the slot being about a width of the chute and a depth greater than a thickness of a set, whereupon the plenum is attached whereby the bottom opening is aligned to the slot such that a set at the bottom opening may drop into a bottom set space in the slot without disturbing plenum-axial alignment or the adjacency of the magnets of the set into the slot;

(d) a first extension of the slot and a straddling edge of a bottom edge of the plenum define a first opening adapted to permit slideable movement of the set in the bottom set space into a further extension of the slot such that the set at the bottom opening may drop into the bottom set space; and (e) means for moving a set in the bottom set space through the first opening.

2. The device of claim 1 wherein a second extension of the slot opposite the first extension and an opposite straddling edge of the bottom edge of the plenum define a second opening adapted to permit slideable movement of a pushing face means into the bottom set space urging the set in the bottom set space into the first extension such that the set at the bottom opening may drop into the bottom set space upon withdrawal therefrom of the pressure face means.

3. A device for delivering planar magnet sets as a substantially horizontal line of adjacent sets comprising:

(a) each set comprising an even number of flat magnets having lateral sides and magnetic poles on top and bottom sides, the magnets arranged adjacently to their lateral sides such that immediately adjacent magnets have opposite magnetic polarities at their top and bottom poles;

(b) a plenum defining a chute with an axis and having a cross section adapted to laterally engage sets of plenum-axially supported sets, the plenum further defining a top and bottom opening of the chute;

(c) a plate defining a slot on an upper surface, the slot being about a width of the chute and a depth greater than a thickness of a set, whereupon the plenum is attached whereby the bottom opening is aligned to the slot such that a set at the bottom opening may drop into a bottom set space in the slot without disturbing plenum-axial alignment or the adjacency of the magnets of the set into the slot;

(d) a first extension of the slot and a straddling edge of a bottom edge of the plenum defining a first opening adapted to permit slideable movement of the set in the bottom set space into the first extension such that the set at the bottom opening may drop into the bottom set space; and (e) means for moving a set in the bottom set space through the first opening to the first extension.

4. The device of claim 1 wherein a second extension of the slot opposite the first extension and an opposite straddling edge of the bottom edge of the plenum define a second opening adapted to permit slideable movement of a pushing face means into the bottom set space urging the set in the bottom set space into the first extension such that the set at the bottom opening may drop into the bottom set space upon withdrawal therefrom of the pressure face means.

5. A device for delivering planar magnet sets as a substantially horizontal line of adjacent sets comprising:

(a) each set comprising an even number of flat magnets having lateral sides and magnetic poles on top and bottom sides, the magnets arranged adjacently to their lateral sides such that immediately adjacent magnets have opposite magnetic polarities at their top and bottom poles;

(b) a plenum defining a chute with an axis and having a cross section adapted to laterally engage sets of plenum-axially supported sets, the plenum further defining a top and bottom opening of the chute;

(c) a plate defining a slot on an upper surface, the slot being about a width of the chute and a depth greater than a thickness of a set, whereupon the plenum is attached whereby the bottom opening is aligned to the slot such that a set at the bottom opening may drop into a bottom set space in the slot without disturbing plenum-axial alignment or the adjacency of the magnets of the set into the slot;

(d) a first extension of the slot and a straddling edge of a bottom edge of the plenum defining a first opening adapted to permit slideable movement of the set in the bottom set space into the first extension such that the set at the bottom opening may drop into the bottom set space;

(e) means for moving a set in the bottom set space through the first opening to the first extension; and (f) an assembly surface substantially horizontal an attached to a top end of the plenum about the top opening to form a substantially rimless path from the assembly surface to the chute, the assembly surface adapted to permit aggregation of sets and delivery thereof to the top opening into the chute.

* * * * *